(12) United States Patent  
Ulbers et al.

(10) Patent No.: US 6,474,815 B1
(45) Date of Patent: Nov. 5, 2002

(54) DEVICE FOR THE STEREOSCOPIC EXAMINATION OF A PATIENT'S EYE

(75) Inventors: Gerd Ulbers, Riggisberg; Hansruedi Widmer, Niederscheri; Eberhard Pertz, Epalinges; Reto Studer, Avenches, all of (CH); David Lobel, Tel-Aviv (IL); Hans Fankhauser, Rapperswil (CH)

(73) Assignee: Haag-Streit AG, Koniz (CH)

( * ) Notice: Subject to any disclaimer, the term of this patent is extended or adjusted under 35 U.S.C. 154(b) by 0 days.

(21) Appl. No.: 09/554,198

(22) PCT Filed: Nov. 11, 1998

(86) PCT No.: PCT/CH98/00480
§ 371 (c)(1),
(2), (4) Date: May 11, 2000

(87) PCT Pub. No.: WO99/23937
PCT Pub. Date: May 20, 1999

(30) Foreign Application Priority Data

Nov. 11, 1997 (EP) .............................................. 97810857
Apr. 29, 1998 (EP) .............................................. 98810380
Sep. 9, 1998 (EP) .............................................. 98810895

(51) Int. Cl.[7] .................................................. A61B 3/10
(52) U.S. Cl. .................................................... 351/214
(58) Field of Search ................................ 351/213, 214, 351/206, 216, 221, 245, 240; 359/368, 375, 376, 382

(56) References Cited

U.S. PATENT DOCUMENTS 4,331,392 A    5/1982  Sato
5,216,456 A    6/1993  Volk
5,424,789 A *  6/1995  Volk ........................... 351/216

FOREIGN PATENT DOCUMENTS

DE    B1133911      7/1962
DE    U1-93084641   9/1993
DE    U1-29514224   7/1995
EP    A1091334     10/1983
EP    A1712600      5/1996

* cited by examiner

*Primary Examiner*—George Manuel

(57) ABSTRACT

The present invention relates to a system for the stereoscopic examination of a patient's eye using a slit-lamp microscope (3), wherein the patient's eye (1) is illuminated by a light strip of a predetermined cross section which is emitted by a light source (5). The light source (5) is arranged on the vertical arm (20) of a support (7) and the eye (1) to be examined is placed in an essentially horizontal plane on one side of said support. The stereo-microscope (3) is essentially placed on a plane which is located on the side opposite to the first side of the support (7). The vertical arm (20) of the support (7) is made in the shape of a column having a narrow cross section so as to minimize the optical obstruction between the stereo-microscope (3) and the patient's eye. Using at least one beam (30b) from the stereo-microscope (3), a partial ray is stopped down and the image information of said ray is directed to a reception unit (44) located in said stereo-microscope (3).

15 Claims, 16 Drawing Sheets

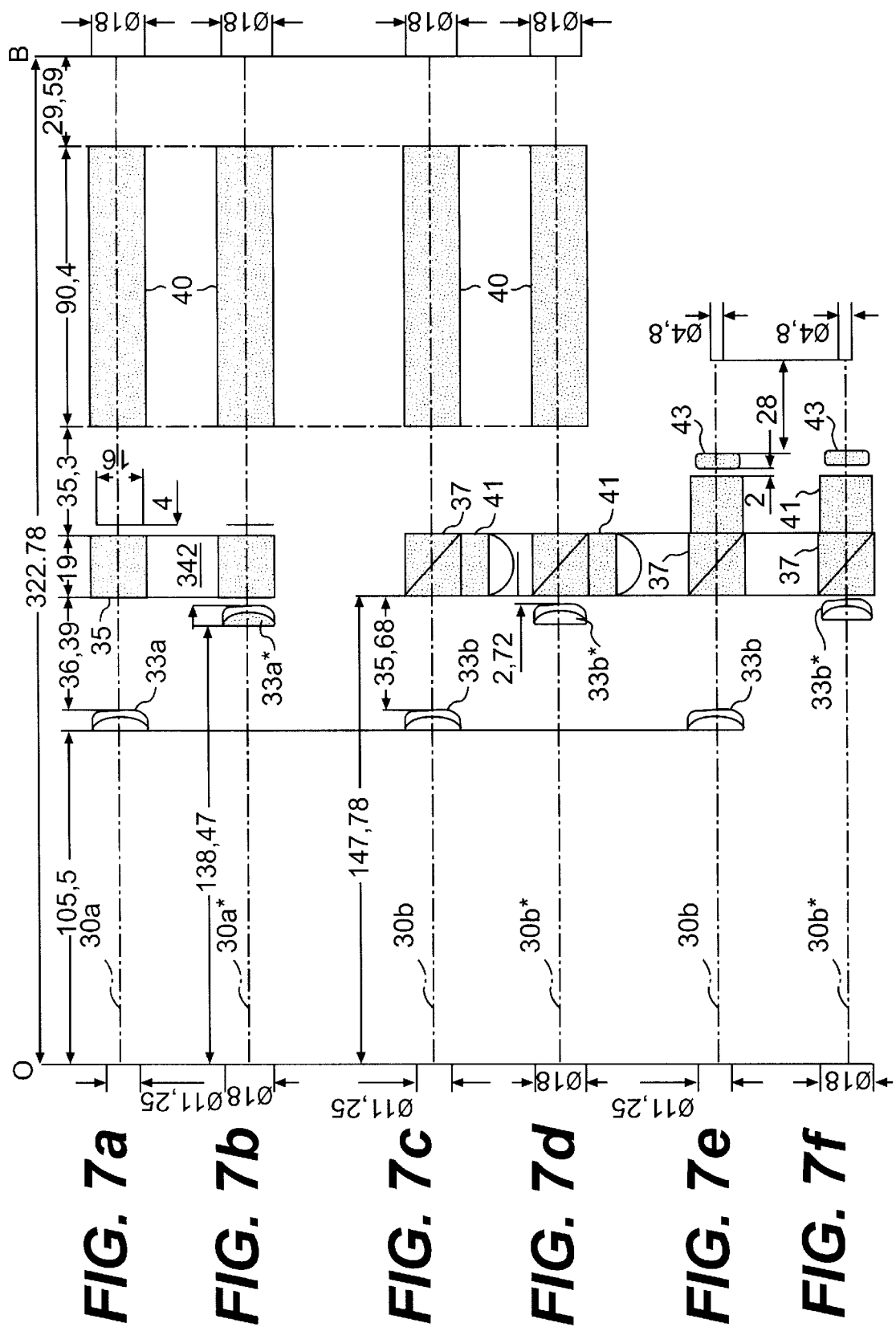

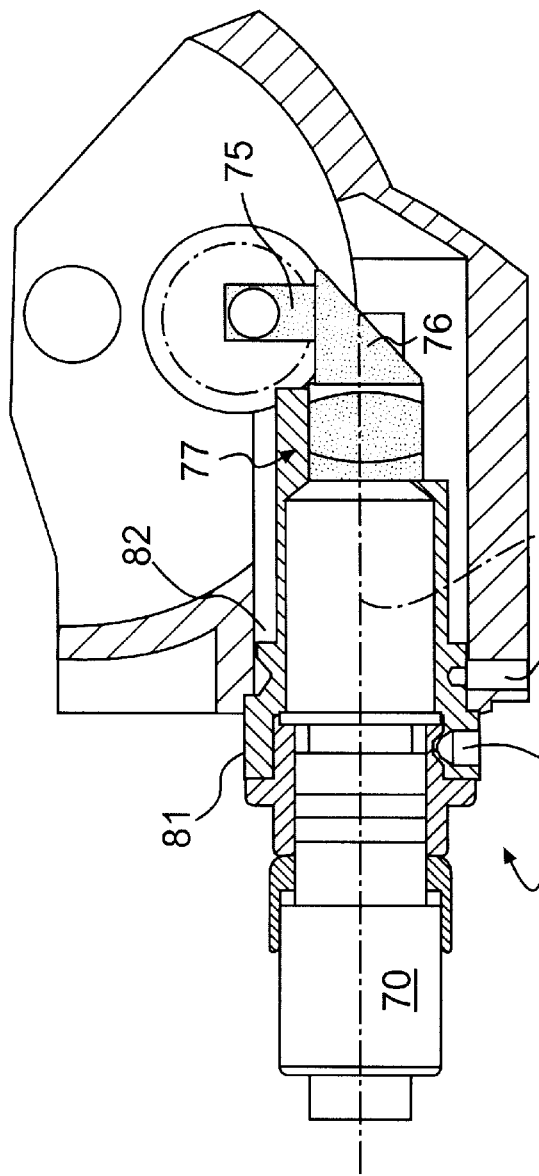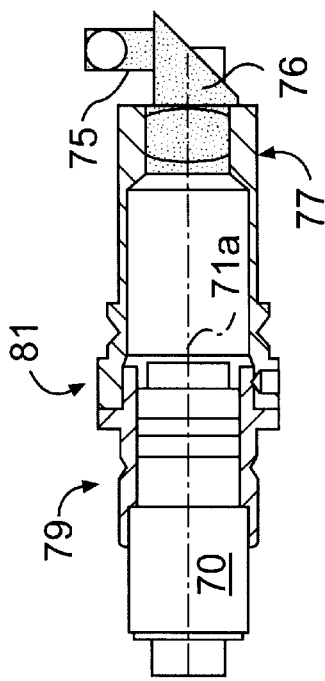
FIG. 9
FIG. 10

DEVICE FOR THE STEREOSCOPIC EXAMINATION OF A PATIENT'S EYE

This application is the national phase under 35 U.S.C. §371 of PCT International Application No. PCT/CH98/ 00480 which has an International filing date of Nov. 11, 1998, which designated the United States of America.

The invention relates to a slit lamp device and a lens supporting unit as an attachment for the device.

BACKGROUND OF THE INVENTION

A slit lamp microscope is known, for example from the company Haag Streit under the name "Original slit lamp 900 BM" and is described with its essential features in DE-A 1 133 911. The known slit lamp device had a viewing unit for stereoscopic examination of the eye and an illumination unit for the eye which is to be examined. The cross section of a illumination spot on or in the eye can be adjusted by a diaphragm which is adjustable in width and height. The illumination unit was located on a vertically running branch of a holding unit. The eye to be examined could be positioned in a roughly horizontally running plane on one side of the holding unit. The viewing unit was located roughly in the plane on the side of the holding unit opposite it. The holding unit had three columns. The illumination optics rested on the two outer columns. On the third middle column which was made as a stub column there was a deflection mirror which guided the beam of the illumination unit to the eye. In the intermediate spaces between one outer column at a time and the stub column the beam paths were guided to the viewing unit.

In U.S. Pat. No. 5,216,456 a three-column slit lamp device is described, the middle column bearing the deflection mirror for illuminating the eye. All three columns are joined via a connecting plate on which then an illumination unit is placed.

In U.S. Pat. No. 4,331,392 the illumination unit is located in the lower part of the slit lamp device and thus necessarily has a construction which is completely different from the invention; in it the illumination unit is located at the top. The arrangement of an illumination unit in the upper part of the slit lamp device compared to the arrangement of U.S. Pat. No. 4,331,392 allows simple replacement of the illumination source. The slit lamp device of U.S. Pat. No. 4,331,392 is foreign to that of the invention and thus not further examined below.

In EP-A 0 091 334 a slit lamp device is described with which the eye could be examined and a laser beam was guided for eye treatment. The slit lamp device of EP-A 0 091 334 was built analogously to that of DE-A 1 133 911, an additional column stub being present for guidance of the laser beam. The analogous structure can be seen especially in FIG. 2 which shows a vertical lengthwise section through the device. FIG. 2 shows cutaway the middle column which bears the deflection mirror. Furthermore, the left side column is shown as seen from the visual field of the patient. The connecting plate for the two side columns on which the illumination unit (here labelled 20) sits is shown cutaway.

SUMMARY OF THE INVENTION

The object of the invention is to devise a slit lamp device which allows good patent-physician contact, ensures efficient examination and which can be economically produced in an aesthetically pleasing form with outstanding optical properties.

The invention is characterized by as little material as possible between the observing and examining physician and the patient in order to ensure efficient examination and good patient-physician contact. A structure which avoids material between the physician and patient is achieved by means of a vertically running branch of a holding unit for an illumination unit made as one column with a narrow column cross section. The narrow column area is preferably made at eye height. Efficient examination is furthermore supported by a video recording. The compact configuration achieved likewise enables economical manufacture. The features of the invention also increase the examination efficiency since the viewing, observing or examining individual need no longer turn his gaze from the viewing unit to look for the controls. The most important controls can be operated with only one hand.

If a Greenough microscope is used as an observation unit preferably in conjunction with the slender holding column as a holding unit, a further reduction in the size of the device results. The video viewing arrangement described below with a Greenough microscope can also be used on other slit lamp devices with the corresponding adaptation. Also the size of the device can be reduced; but its mass does not decrease as much as when using the single-column holding unit.

One partial beam which is guided to a recording element of a recording unit is masked out into one of the two beam paths of the Greenough microscope for display and evaluation purposes. If the decoupling of the partial beam as was the case in conventional slit lamp devices, having a different microscope than a Greenough microscope, were to take place, much larger dimensions would result.

The structure described below furthermore easily allows integration of optical filters which enable better observation results.

In one preferred version, a lens supporting unit can simply be slipped on as an accessory. With this accessory part, studies can be done on the vitreous body and on the ocular fundus. These examinations have been done in the past with a so-called "movable Hruby adapter glass". This means had a rod on which one examination lens was arranged with a capacity to swivel. The rod had a vertically running guide rod which was guided in the direction of the patient in one slot on the slit lamp device. This guide rod led through an attachment plate which was attached to the chin holder for the patient's head. Directly underneath the lens there was a small lever as the handle for moving the lens. The examinations performed with the known "adapter glass" were often not reproducible since when the lever was released generally the lens moved. Photographs for documentation were thus hardly possible.

Embodiments and other advantages of the invention are described below.

BRIEF DESCRIPTION OF DRAWINGS

The following examples of the device and the slit lamp microscope are detailed using the drawings.

FIGS. 7a to 7f show two embodiments of arrangements of optical components and their distances in the two beam paths of the Greenough microscope which is shown in FIGS. 5 and 6, the reference numbers corresponding to those in the Figures, the numerical data are in millimeters. O' is the object plane without a protective glass 31, B is the image plane for visual examination and Bv is the image plane of the video recording element 44; FIGS. 7a, 7c and 7e shown the location of optical components for one enlargement and FIGS. 7b, 7d and 7f for the others, FIG. 9 shows a cross section along the section line IX in FIG. 8 for representation of the behavior of the partial beam which is decoupled from one of the observation beams and which is guided onto a video recording element of a video recording unit, FIG. 10 shows a cross section through the video recording unit which is shown in FIG. 9 as a separate component.

DETAILED DESCRIPTION OF THE INVENTION

Figure 1:
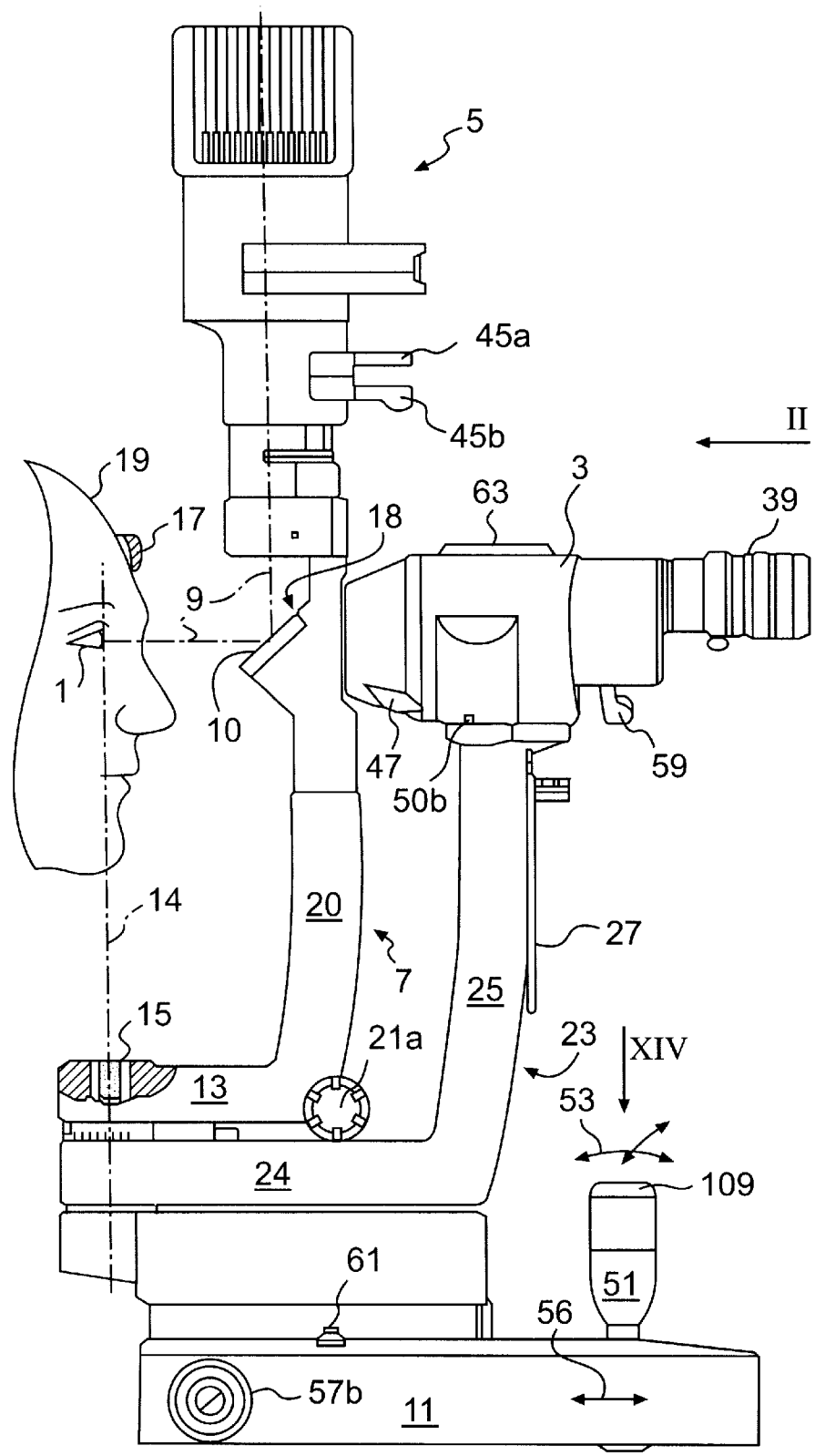
FIG. 1 shows a side view of the slit lamp device with assignment to the human eye, here the video recording unit 46 which is shown by way of example in FIG. 6 not being used and therefore the housing opening being closed with a plug 50b.
Figure 2:
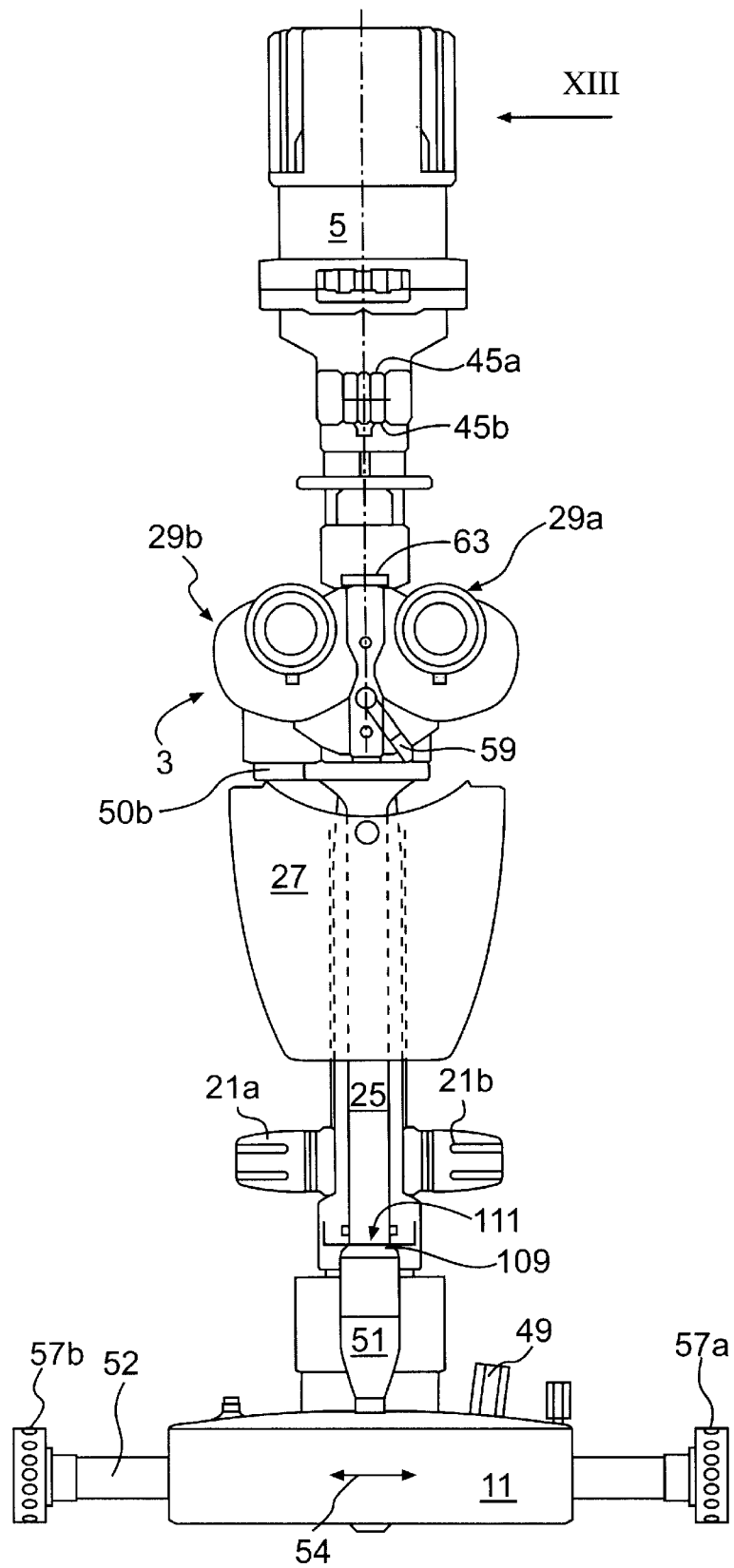
FIG. 2 shows a view of the slit lamp device which is shown in FIG. 1, a view turned 90° around a vertical axis, in the direction of viewing II there.

The slit lamp device which is shown in FIGS. 1 and 2 as a device for stereoscopic examination of an eye 1 has a viewing unit 3 and an illumination unit 5. The viewing unit 3 is held with a holding unit 23 and the illumination unit 5 is held with a holding unit 7. As is detailed below, the illumination unit 5 can be used to produce a light beam 9 as radiation which can be guided via a deflection mirror 10 which is located on the holding unit 7 into or onto the eye 1. The cross section of the light beam 9 can be adjusted according to the details below, especially as a thin streak of light. The holding unit 7 is located on a foot 11 of the device to be able to swivel via a swivel unit with a vertical swivel axis.

Figure 3:
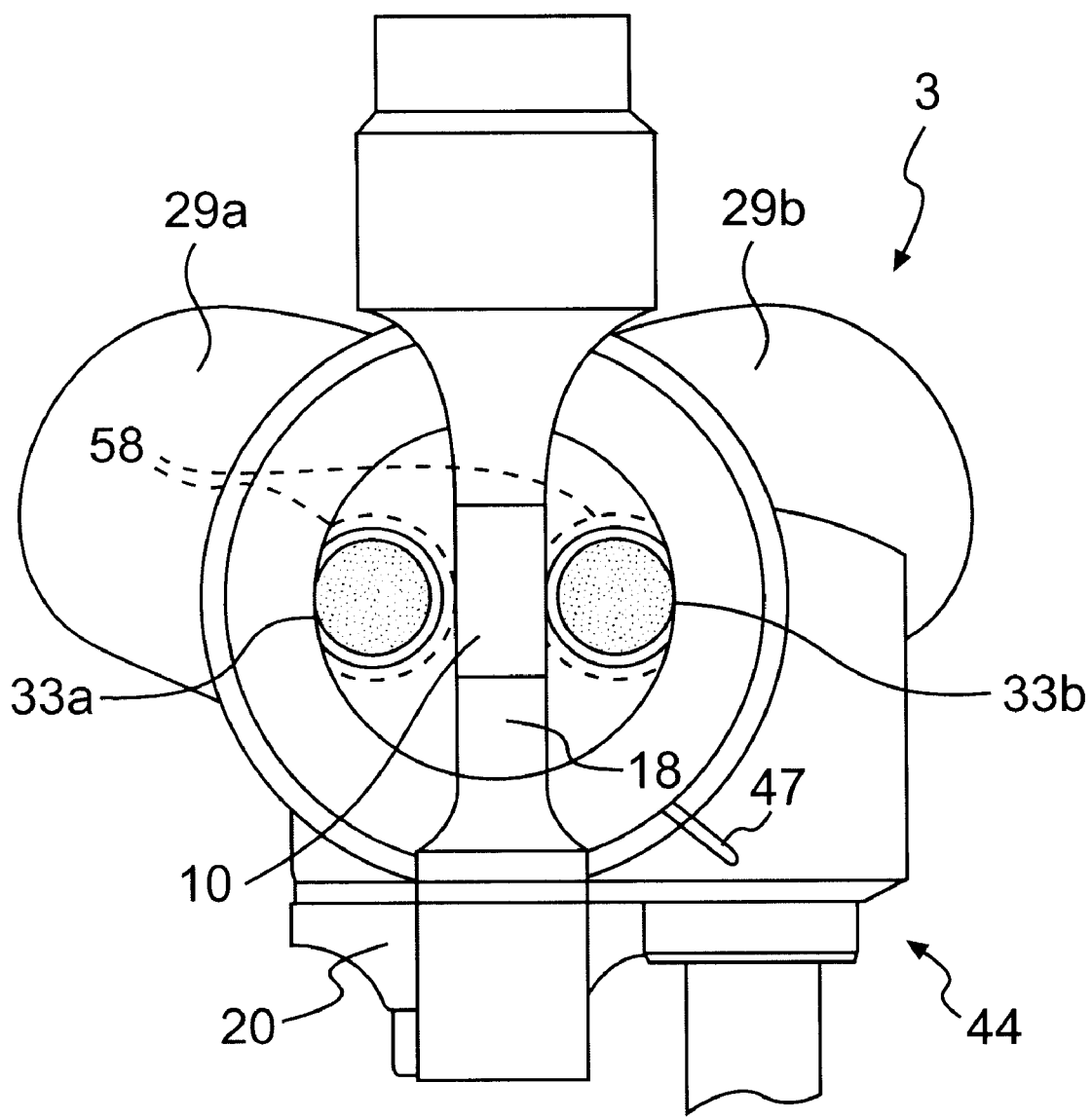
FIG. 3 shows an overhead view proceeding from the patient's eye to a holding unit of the slit lamp device which is shown in FIGS. 1 and 2.

The holding unit 7 is made as a L-shaped component which is located with a swivelling capacity on the foot 11 of the device on the end of a horizontally running leg 13 in a swivel joint 15 which can be swivelled around a vertical axis 14. The location of the axis 14 is chosen such that it runs past the front of the eye for a human forehead which is placed against a (only suggested in the drawings) forehead band 17 of a head holder (not shown). The other leg 20 of the L-shaped holding part 7 runs vertically and, as stated above, is made as a single column. So that between the viewing unit 3 and the eye 1 of the patient there is only slight optical distortion, a single column is used as shown in FIG. 3. In the area of the eye height of the patient the horizontal cross section of the holding unit 5 is greatly reduced. There is a deflection mirror 10 on this area 18 which reduces the cross section. The cross section is made as narrow as possible. The reduction of the horizontal cross section is limited by mechanical stability constraints and the width of the deflection mirror 10 which is necessary for illumination beam guidance. Furthermore guidance of the elements described below within the leg 20 which is made hollow inside militates against any reduction in the width of the area 18.

In its cavity a rod-shaped adjustment mechanism (not shown) runs for adjustment of the slit width in the illumination unit 5 which is located on the top end of the leg (20). The rod-shaped adjustment mechanism (not shown) acts with a cam which is not shown and which lies within the holding unit 7 in its external area of the union between the two legs 13 and 20. On each of the two ends of the cam there is a adjustment knob 21a and 21b. The surface of each adjustment knob 21a and 21b can be easily gripped.

The viewing unit 3 is likewise located on an L-shaped holding unit 23 analogously to the illumination unit 5. This holding unit 23 also has one horizontally and one vertically running leg 24 and 25. The end of the horizontal leg 24 is swivel mounted around the vertical axis 14 analogously to the holding unit 7 and with the swivel joint 15 which is elongated downward is swivel-mounted on the foot 11 of the device independently relative to the holding unit 7. On the outside of the leg 25 a breathing protection shield 27 is interchangeably held. On the top end of the leg 25 the viewing unit 3 is located at a height which makes it possible to look into the eye 1.

Figure 4:
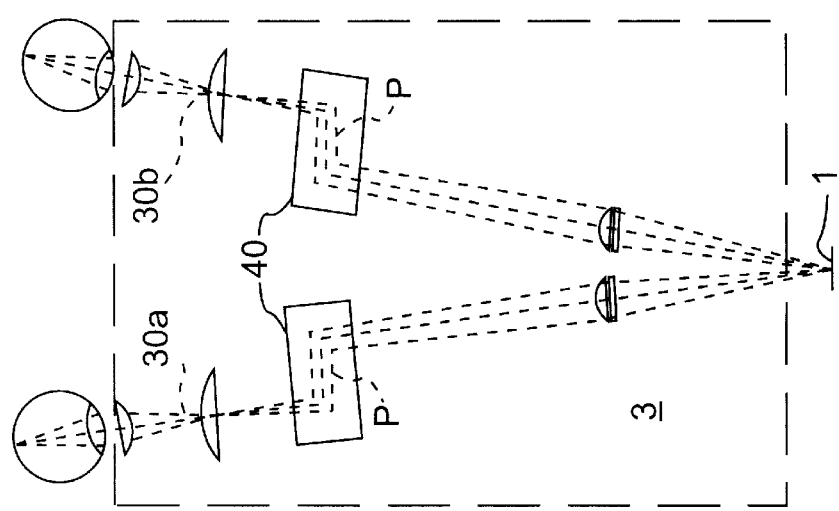
FIG. 4 shows a schematic of known Greenough microscopes.

The viewing unit 3 is fundamentally made as a Greenough microscope. The fundamental structure of this stereomicroscope is shown in FIG. 4 as a sample figure from Karl Muetze, "ABC of Optics", key word "Stereomicroscopy", 1961, Verlag Werner Dausin, Hanau/Main. According to this reference a Greenough microscope is used for direct three-dimensional viewing. It has two separate microscopes which are tilted by an angle of 14 to 16° against one another, this angle corresponding roughly to the angle of convergence of the human eye axes when viewing an article from the distance of the conventional field of vision of 25 cm. A set of Porro prisms P of the first or second type aligns the image so that it is seen in the same location as the object. This is necessary to obtain an orthoscopic (with correct depth) image.

Figure 5:
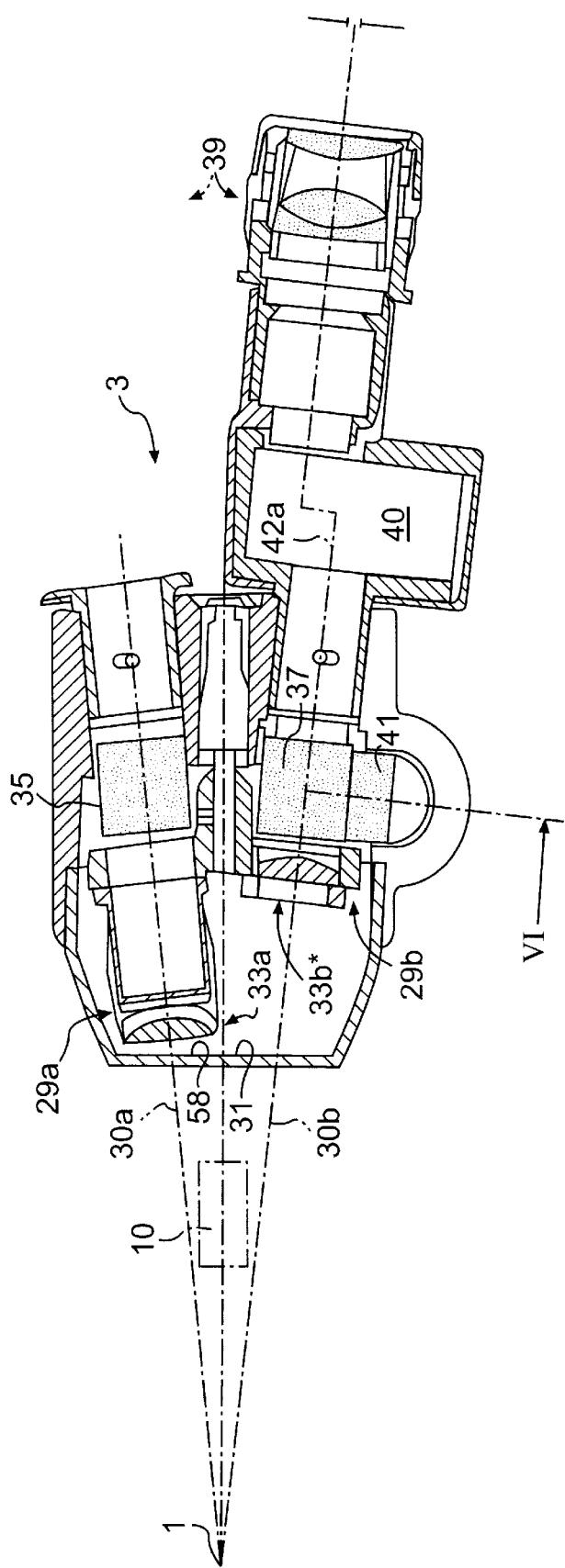
FIG. 5 shows a cross section through the modified Greenough microscope used in the device from FIGS. 1 and 2 as a viewing unit, here in a single figure two different layers of optical components being shown for one different enlargement each.

In a Greenough microscope the objectives are very close to one another, by which according to the statements in the aforementioned citation high apertures are not possible. The device as claimed in the invention is different from a typical Greenough microscope, as is shown by the cross section in FIG. 5. FIG. 5 shows the two individual microscopes 29a and 29b which are separated from one another in a cross section tilted towards one another at an angle of 13°. The beam paths of the individual microscopes 29a and 29b are labelled 30*a* and 30*b*. In the top part of the figure the location of the optical components is shown for one enlargement scale and in the lower half of the figure for another. The enlargement scales are switched with the switch lever 59 which can be seen in FIG. 2.

At the observation beam inlet into the Greenough microscope 3 there is a single protective glass 31 for the two beam paths 30*a* and 30*b* in front of the two objectives 33*a* for the one enlargement scale and in front of the two objectives 33*b* for the other enlargement scale. In the "upper" beam path 30*a* a plane-parallel plate 35 for optical matching to the splitter prism 37 which is downstream of the objective 33*a* in the "lower" beam path 30*b* follows the objective 33*a*. The "upper" and the "lower" beam path are the left and right beam path as shown in FIG. 2. The plane-parallel plate 35 is followed by a Porro prism 36 which is upstream of an eyepiece 39, especially an interchangeable eyepiece. Both components are shown only in the "lower" beam path.

In the beam path 30*b* there is image decoupling for a video recording unit 46. This is done with a splitter prism 37 which divides the beam path 30*b* into one component beam 42*a* via the Porro prism 40 to the eyepiece 39 and into another component beam 42*b* via a deflection prism 41 and a video objective 43 to a recording element 44 of the video recording unit 46. The video recording unit 46 consists of a splitter prism 37, the deflection prism 41, the video objective 43 and the video recording element 44. The video recording element 44 is held in a mount 48*a* which plugs in an adjustment sleeve 48*b*. The mount 48*a* is held with a clamp screw 48*c* in the adjustment sleeve 48*b*. The adjustment sleeve 48*b* sits in a housing hole 50*a* with the capacity to turn and to be displaced and can be fixed with clamp screws 48*d* which fit in a peripheral groove on the outside jacket of the calibration sleeve 48*b*. The optical image can be adjusted by moving the mount 48*a* and the calibration sleeve 48*b*. So that no dirt can penetrate through the housing hole 60*a*, this is closed by a removable plug 50*b*. The video recording unit 48 can be interchanged as a whole. Likewise the video recording element is interchangeable.

Figure 6:
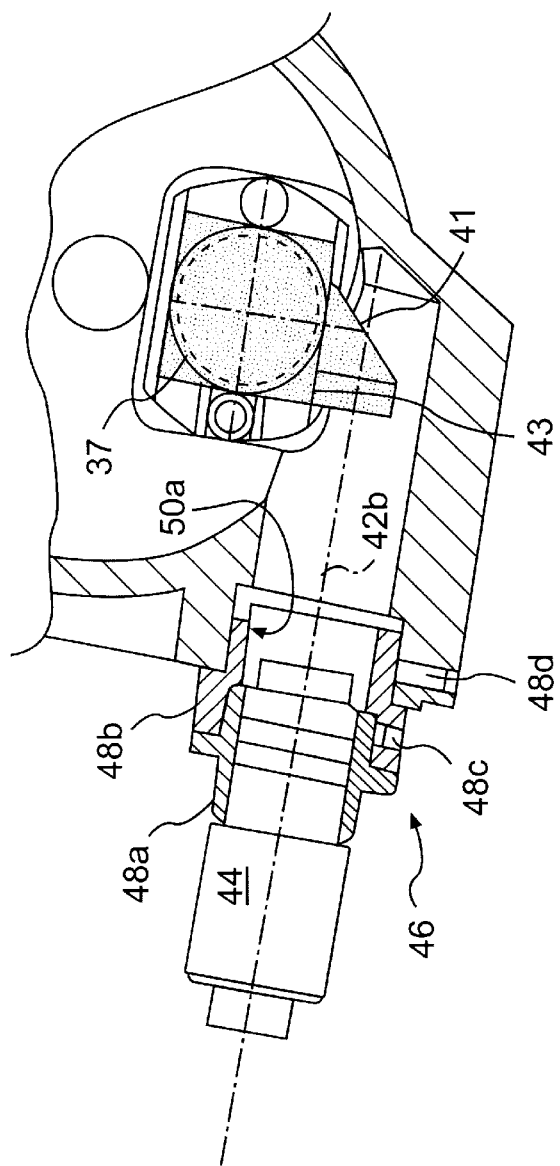
FIG. 6 shows a cross section along the section line VI through one beam path of the Greenough microscope shown in FIG. 5 for representation of an arrangement of a video recording unit, to the recording element of which the one partial beam of this beam path is guided.

In addition to visual examination, video photographs can thus also be taken for direct observation or for recording (documentation). The arrangement of the recording unit 44 is shown in FIG. 6.

FIGS. 7*a* and 7*f* show two optical versions for different enlargement scales. FIGS. 7*a*, 7*c* and 7*e* show a version with one objective 33*a* and 33*b* each with 1.6× enlargement and in the video beam path with one objective 43 with likewise 1.6× enlargement.

In the other version which is shown in FIGS. 7*b*, 7*d* and 7*f*, the components which are different from those in FIGS. 7*a*, 7*c* and 7*e* are labelled with an apostrophe '. In this version one objective 33*a*' and 33*b*' each with 1:1 imaging and in the video beam path with one objective 43' with the same enlargement are used. Other versions are of course possible.

The illumination unit 5 has two levers 45*a* and 45*b* which can be swivelled around a horizontal axis and which are arranged on top of one another. With these levers 45*a* and 45*b* the height and the width of a diaphragm opening can be adjusted. The cross section of this diaphragm opening defines the cross section of the thin streak 9 of light which is to be aimed at the eye 1. With these two levers, additionally a blue or gray filter can be swivelled into the illumination beam path 9 and out again. The swivelling in and out takes place in the end region of the swivelling process of the pertinent lever 45*a* and 45*b*.

Likewise a yellow filter 58 can be placed in the beam paths 30*a*, 30*a*', 30*b*, and 30*b*' with an adjustment device on the viewing unit 3. The yellow filter 58 here consists of two partial vapor depositions on the inside of the protective glass 31. With the adjustment device 47 the protective glass 31 can be turned so that the two partial vapor depositions 58 lie on the one hand in front of the objective 33*a* and 33*b* (in the beam paths 30*a* and 30*b* as is suggested in FIGS. 3 and 5) and on the other next to them (not in the beam path 30*a* and 30*b*).

If fluorescein is applied to the surface of the eye for example when a contact lens (not shown) is inserted, and is illuminated with blue light (blue filter folded down), yellow fluorescence occurs which can be easily observed with a Greenough microscope 3 when there is a yellow filter in the observation beam path (check of fit of contact lenses).

On the viewing unit 3 there is a switching lever 59. With this switching lever 59, depending on the desired enlargement, the objectives 33*a* and 33*b* and 33*a*' and 33*b*', as are shown in FIGS. 7*a*, 7*c*, and 7*c*, can be alternately swivelled in the beam paths and then in the other lever position those of FIGS. 7*b*, 7*d* and 7*f* can be swivelled. FIGS. 7*e* and 7*f* shown the beam behavior in a position swivelled relative to FIGS. 7*a* to 7*d* by 90°. On the foot 11 of the device there is furthermore a power connection 61 for the light source in the illumination unit 5 and for the recording unit 44.

To observe the entire visual field, underneath the deflection mirror 10 which is arranged at 45° there is a cold light guide which is not shown. Furthermore a tonometer for measuring the eye pressure can be placed in an adapter 63 on the housing of the Greenough microscope. The brightness of the "slit lamp" in the illumination unit 5 is adjusted by a manual controller 49 which is located on the foot 11 of the device. The electrical cable for brightness control or power supply runs within the hollow holding unit 7. The positioning of the device horizontally in the X direction and the Y direction is done using a guide lever 51 which is located on the foot 51 of the device, often also called a "joystick". By lateral deflection 53 the foot 11 of the device can be moved laterally on an axis 52 in the Y direction 54. Movement in the X-direction 56 is also possible by swivelling 55 of the guide lever 56 forward and backward. The movement in the X-direction takes place via rotary motion of the wheels 57*a* and 57*b* which are located on either side on the axis 52 and which roll off on rails which are not shown and which are attached to a base which is not shown. On this base there is also a head holder which is not shown and which has a forehead band 17.

The guide lever 51 can furthermore be turned around its vertical axis. In order to achieve a good turning capacity, the coupling lever 51 is provided in its top jacket area with peripheral ribbing. The turning causes synchronous vertical adjustment of the holding units 7 and 23 and thus a vertical adjustment of the thin streak 9 of light which is to be directed into the eye 1 together with the viewing unit 5.

Since the leg 20 of the holding unit 7 can be made very slender, for reasons of manufacture the laying the power cable in it can be abandoned. The power supply in this case passes to the power connection 61, from the latter to the manual controller 49 and from it back again to the power connection 61 and from it then via an external (cable which is not shown) via the (head support which likewise is not shown) into the illumination unit 5.

Figure 8:
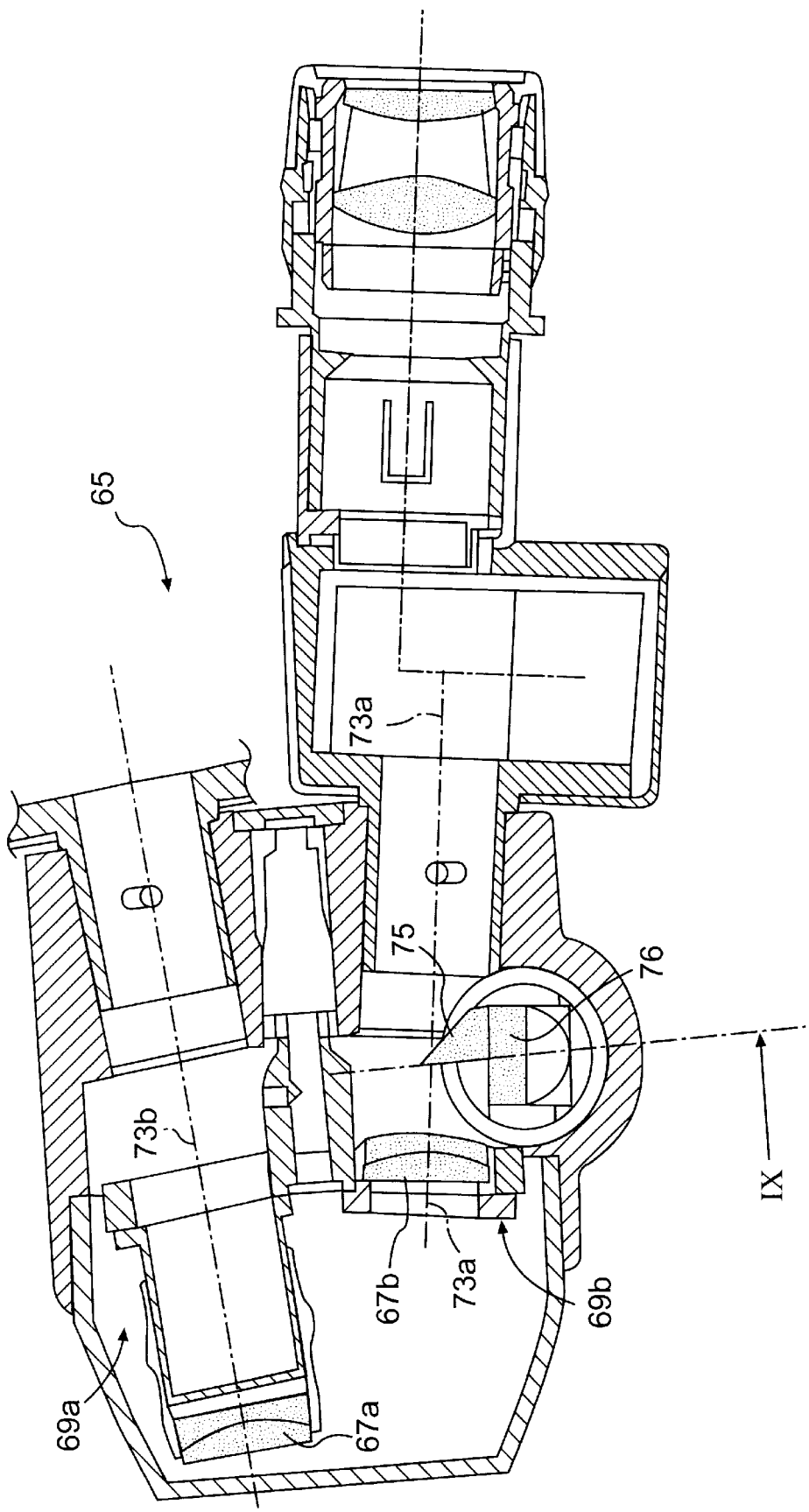
FIG. 8 shows one version of the viewing unit shown in FIG. 5.

Instead of decoupling for the recording unit 44, as described above, with partially transparent components for example via the splitter prism 37, only a fraction of the beam cross section can also be decoupled using a decoupling mirror or a decoupling prism, as is shown for example in FIGS. 8 to 10. FIG. 8 shows one version 65 of the viewing unit 3 (Greenough microscope) which is shown in FIG. 5. The input objectives 67a and 67b of the individual microscopes 69a and 69b and their location are made analogously to the objectives 33 and 33b' in FIG. 5. Since decoupling of a component beam 71a takes place to a video recording element 70 which is made analogously to the video recording element 44 (visible in FIGS. 9 and 10) by decoupling a fraction of the incident beam 73a (analogously to beam 30b), optical compensation by a plane-parallel plate analogous to plate 35 is not necessary. In this way the structure of the viewing unit 65 is greatly simplified compared to the viewing unit 3.

To decouple a component beam 71a a prism 75 is used which partially projects into the cross section of the beam 73a. The decoupled component beam 71a is deflected one more time with a second prism 76 and is imaged with imaging optics (video objective) 77 on the receiving plane of the video recording element 70. The video recording unit 79 here consists of a prism 75 which geometrically decouples a component beam, a prism 76, imaging optics 77 and the video recording element 70.

The video recording unit 79 (camera) which is shown in FIGS. 9 and 10 can likewise be replaced as a whole, but also only the video recording element 70 alone can be replaced. The prisms 75 and 76, the imaging optics 77 and the video recording element 70 are located and held in a housing 81 which with optically fitting can be pushed into the housing opening 82 of the viewing unit 65 such that the prism 75 comes to rest correctly in the beam 73a for decoupling of the component beam 71a. Also here are there shifting and turning of the video recording element 70 to adjust the image. The housing 81 (FIG. 9) analogously to FIG. 6 likewise has a mount for the video recording element 70 and an adjustment sleeve. Fixing takes place here as well with the clamp screws 83a and 83b. By means of the interchangeability of the video recording unit 79 the viewing unit 65 with this video recording unit 79 can be easily refitted among others in terms of salesmanship. Furthermore, after removing the video recording unit 79 the image contrast in both observation beam paths 73a and 73b is the same. The viewing unit 65 can be produced more easily and thus also more cost favorably compared to the viewing unit 3.

Figure 11:
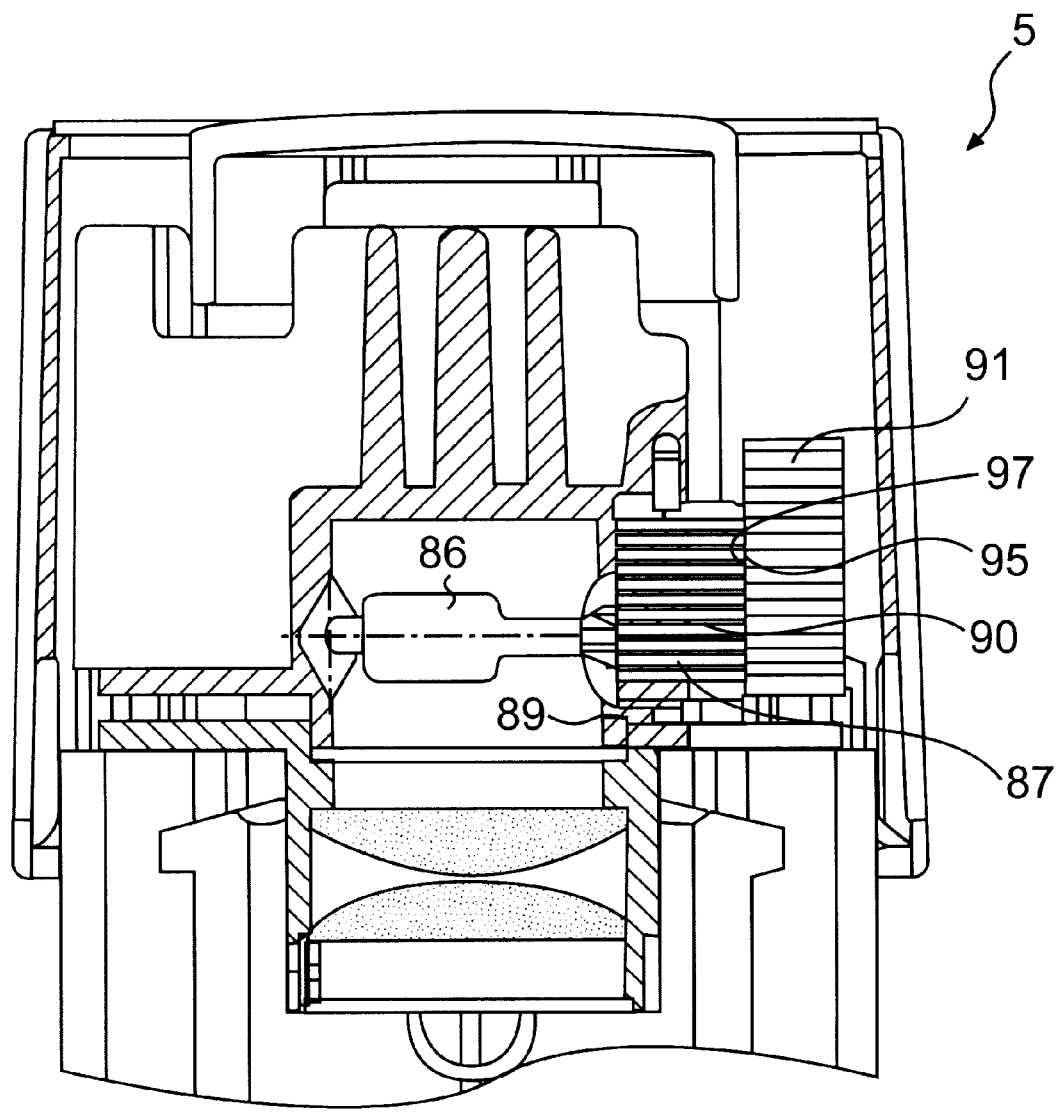
FIG. 11 shows a cross section through an illumination unit of the slit lamp microscope which is shown in FIG. 1.
Figure 12:
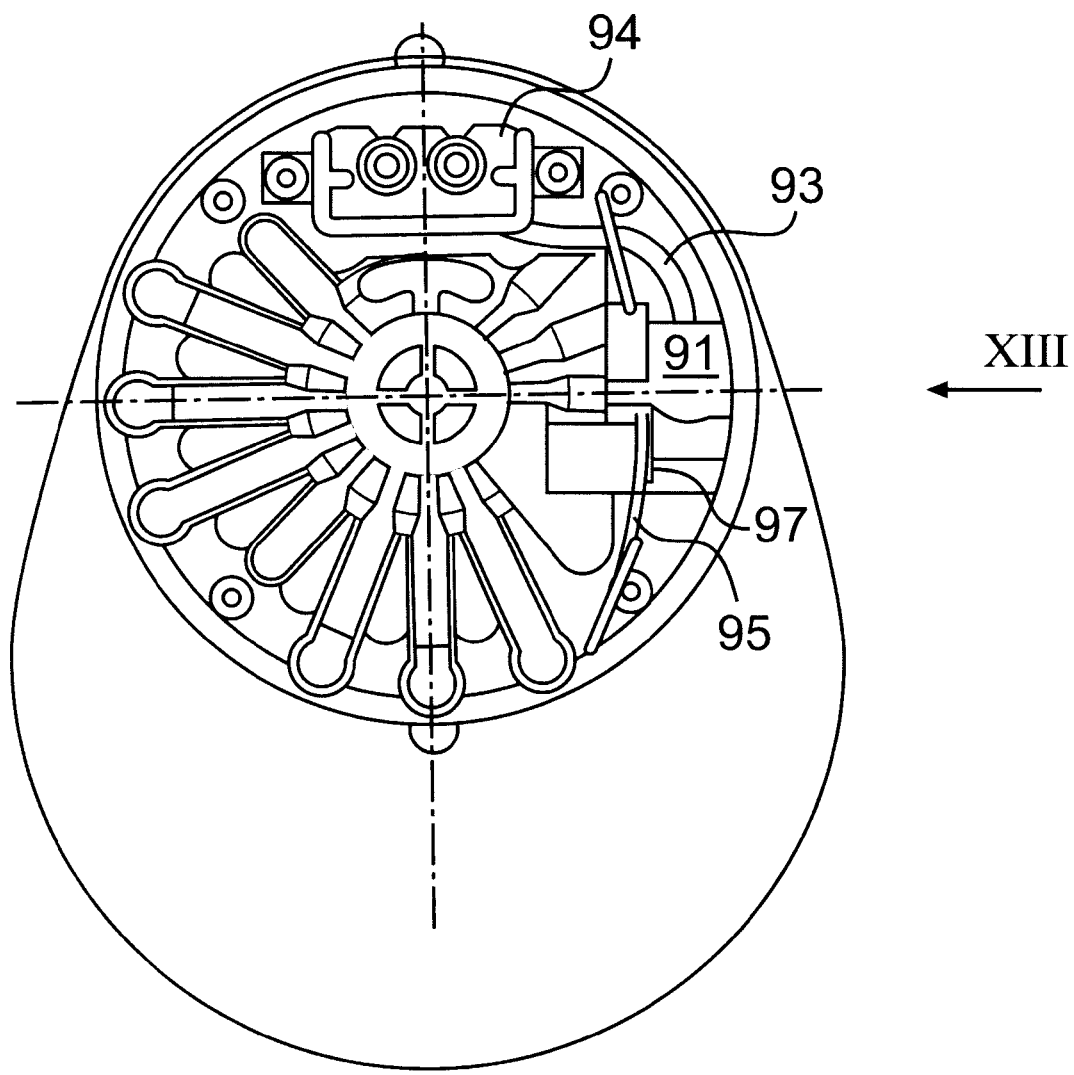
FIG. 12 shows an overhead view of the illumination unit which is shown in FIG. 11.
Figure 13:
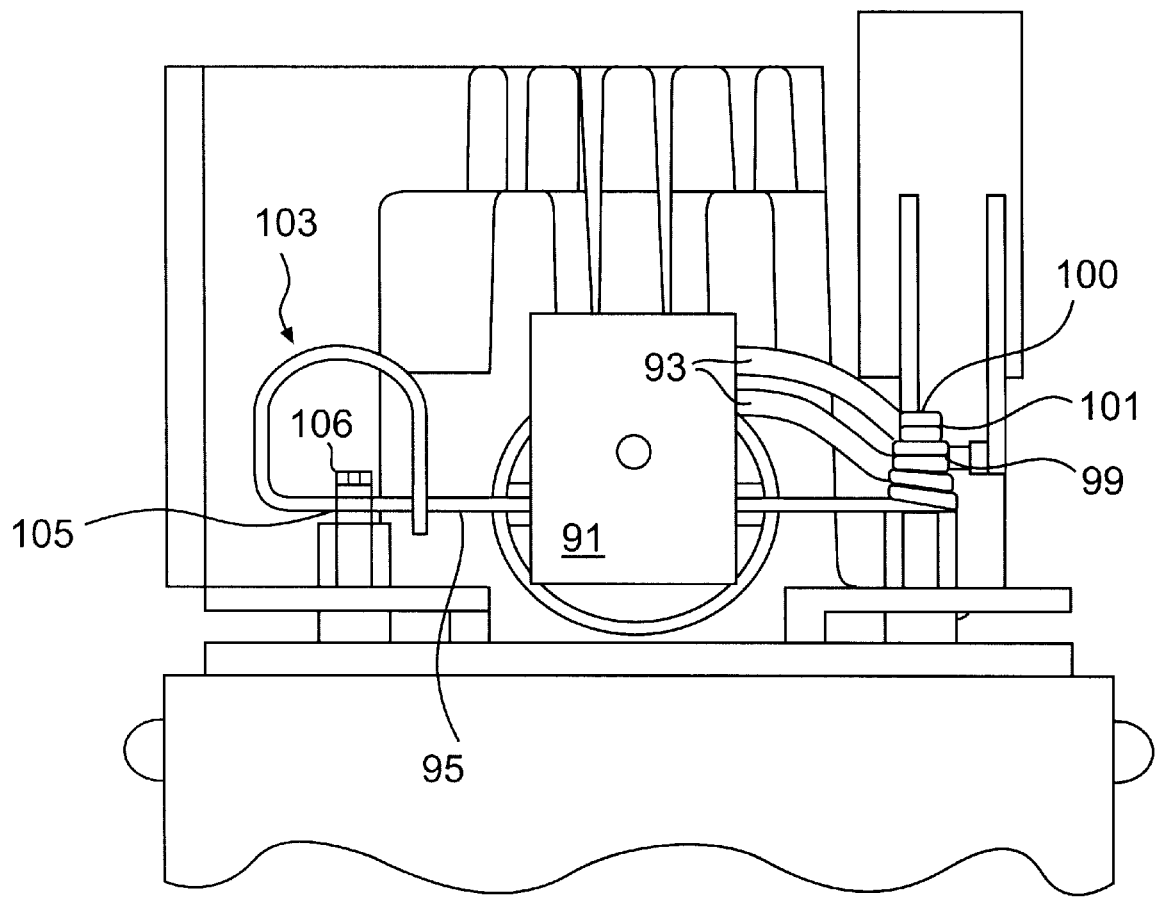
FIG. 13 shows a side view of the illumination unit with the viewing direction XIII shown in FIGS. 2 and 12.

The arrangement of a light source 86 which is inserted into the illumination unit 5 is shown in FIG. 11 in an enlarged cross section. As the light source 86 a so-called high temperature quartz lamp can be used which is held interchangeably in a fitted base 87. The base 87 sits with a clearance fit in a sleeve 89. The base 87 has contact pins 90 which fit into matching sleeves of a plug piece 91 which can be removed from the base 87. From the plug piece 91 a cable 93 passes to an electrical connection piece 94. The base 87 is kept from sliding out with an elastic clip 95 of spring wire which lies in a groove 97 of the base 87. The clip 95 is wound roughly in a circular cylinder on its one side, with for example five turns here, forming a "tube piece" 99. The "tube piece" 99 slips onto a pin 100 with a top end which bears a clamp disk (Seeger circlip ring 101) which prevents the "tube piece" 99 and thus the clip 95 from sliding out.

The other end of the clip has a pull loop 103 which can be inserted into a peripheral groove 105 in the top of a pin 106. The clip 95 is elastically pre-bent such that it presses the base 87 into the sleeve 89 and itself presses against the groove 105. To replace the light source 86 the plug piece 91 must be withdrawn and then the pull loop 103 must be raised only over the upper end of the pin 106. The light source 86 can now be withdrawn with the base 87. So that the base 87 can be easily grasped, it projects somewhat over the outer edge of the sleeve 89.

The advantage of the arrangement for holding the light source is its simple configuration. Furthermore, a tool is not required for changing the light source.

Figure 14:
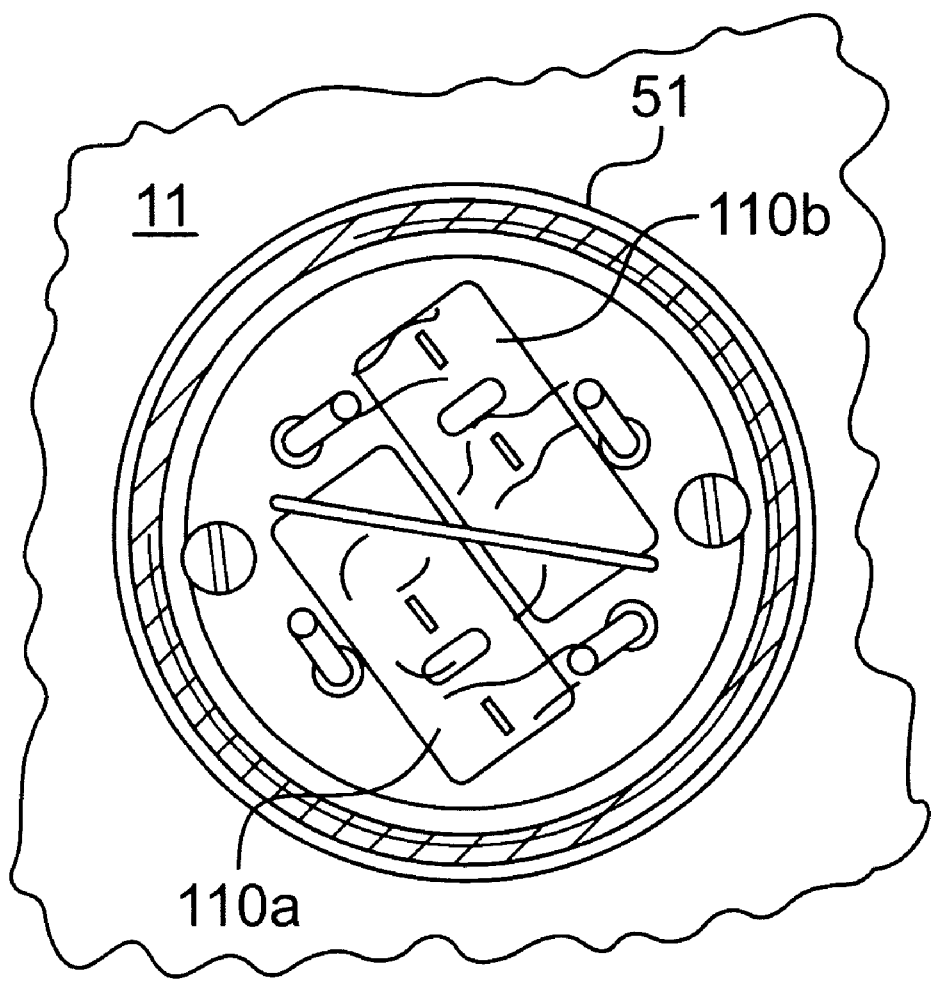
FIG. 14 shows an overhead view of a guide lever of the slit lamp device in the viewing direction which is shown in FIG. 1, the cover on the upper part of the guide lever being removed.
Figure 15:
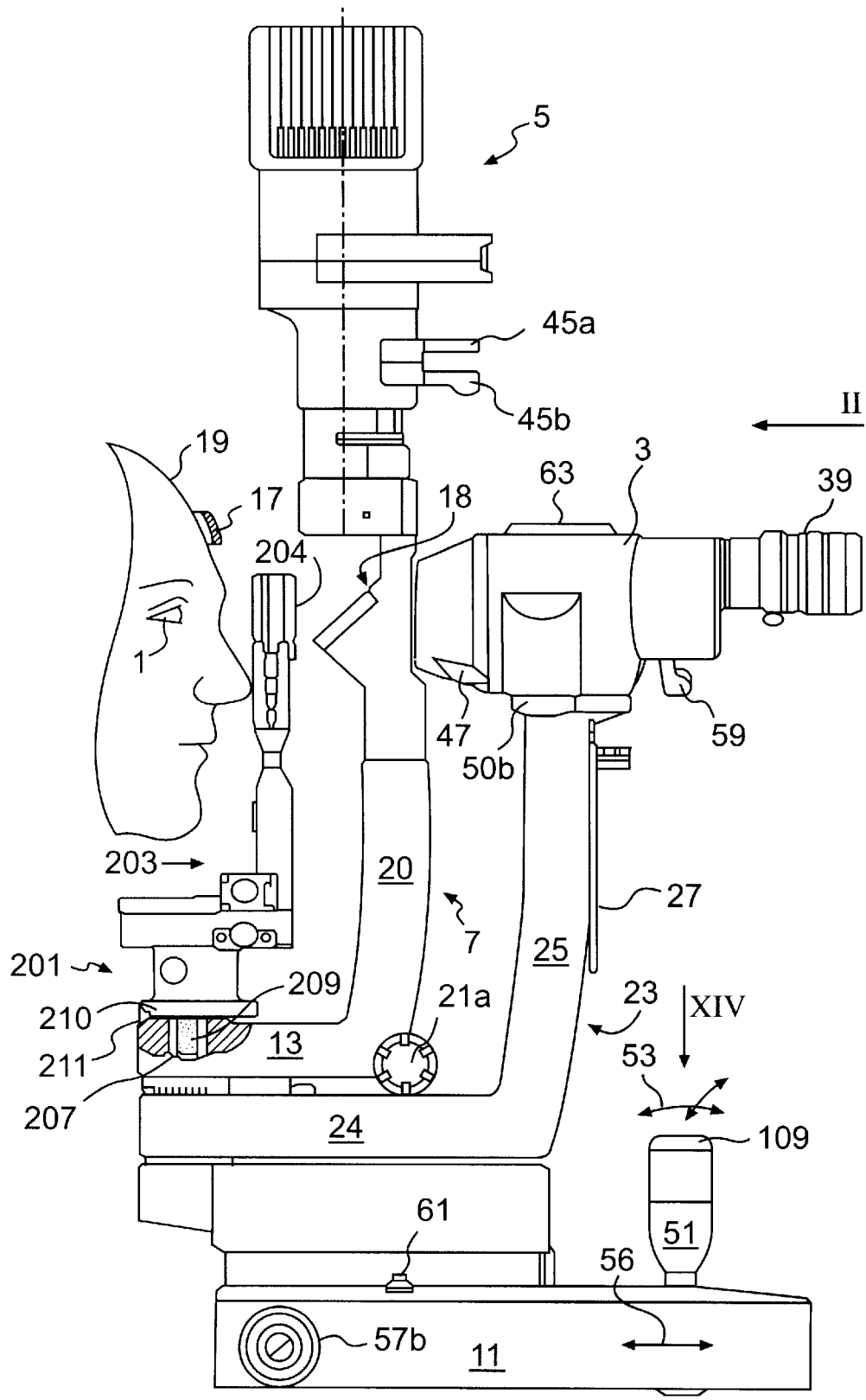
FIG. 15 shows the slit lamp device which is shown especially in FIG. 1 with a removable lens supporting unit.

In the top part 109 of the guide lever 51, as indicated in FIG. 14, there are switching elements 110b and 110b for control of the functions of the device or of the functions which control peripheral units which are connected with the viewing device. In the embodiment shown here in the upper part 109 as the switching elements there are two microswitches 110a and 110b (toggle switches, . . . ) next to one another as signal-delivering elements. The two microswitches 110a and 110b can preferably be operated from the top 111 of the top part 109 preferably with the thumbs. If the device is to be used in a rough environment, the top 111 is covered to be splashproof by an elastic film.

Instead of microswitches, pushbuttons or momentary-contact tumbler switches can also be used. If for example the top part of the switch 110a which is made as a momentary-contact tumbler switch is pressed, for example via a motor drive which is not shown, the light slit width of the light source can be reduced. If then the lower part of the switch 110a is pressed, the slit would be enlarged. This function would eliminate manual operation of the adjustment knobs 21a/b by another hand. Via the switch 110b brightness could be controlled in a similar manner; this would result in elimination of adjustment via the manual controller 49. The treating physician can then continually view without having to glance at these adjustment elements. Also here the physician has the hand required previously for adjustment free for treatment manipulations.

With these two switches/momentary-contact tumbler switches 110a/b other units can be adjusted. Electrical and signal-engineering connection could take place via the terminal 61 or via a separate terminal which is not shown. For example a tonometer could be moved against the surface of the eye.

By actuating the two switches/momentary-contact tumbler switches 110a/b adjustments can be made using motorized drives. So that at this point the physician knows in which position the pertinent unit or the slit width or the brightness is found, reflecting the data into the beam path of the viewing unit 3 or 65 can be done. The reflection-in would take place now analogously to beam reflection out for the video recording element 44 or 70. Instead of the video recording element 44 or 70 there would be only one display element with video information which is being reflected in. Then the prism 37 and 75 can be turned 180° relative to the representations in FIGS. 5 and 8 for reflection-in.

If the slit lamp device is also to be used for preferred examination of the vitreous body and the ocular fundus of the patient, the device with a lens supporting unit 203 which can attached and removed again without using tools manually via a coupling 201 is placed with an examination lens 204 in front of the inlet of the observation beam in the viewing unit 3 in the observation beam path, therefore in front of the protective glass 30. The examination lens 204 is held self-locking with a turning capacity and self-locking in all three-dimensional directions with an adjustment capacity with the lens supporting unit 203. The lens supporting unit 203, in contrast to the known Hruby adapter glass which can be used together with a slit lamp, has no mechanical connection to the head holder and chin holder of the patient.

The lens supporting unit 203 has a plate-shaped support part 205 from which a cylindrical stud 207 projects. The cross section of the stud 207 is chosen such that it can be inserted with a clearance fit into an axial hole 209 which is shown in FIG. 1. The axial hole 209 is formed centrally to the vertical axis of the swivel joint 15. With the swivel joint 15 the holding part 7 for the illumination unit 5 and the holder 23 for the viewing unit 3 can be swivelled. The pin 207 and the axial hole 209 for a plug coupling 201. Locking of the lens supporting unit 203 is achieved by the plate edge of the support part 206 being provided with a notch 210. In the inserted state the projecting part of a sheet strip 211 which is located on the front of the horizontal leg 13 of the holding unit 7 fits into this notch 210. The support part 205 in an extension upward has a roughly cuboidal base part 213; on its horizontal top a first carriage 214 is positioned to be movable in the lengthwise direction of the cuboid (in the installed state in the direction towards the patient's eye 1 and away from it). The carriage 214 is guided on the base part 213 for example in a dovetail guide which can be fixed with a clamp screw 215 which is provided with knurling for better grip. When the clamp screw 215 is loosened, movement by hand is possible. With this guide coarse adjustment of the distance of the lens 204 from the patient's eye 1 can be done. On the first carriage 214 there sits a second carriage 217 which can be moved in the same direction as the first carriage 214. The movement takes place however via a likewise knurled fine adjustment screw 219. Horizontally, perpendicularly to the first and the second carriage 214 and 217 there is a third carriage 220 which can be moved likewise via a fine adjustment screw 221 by turning it. With the two fine adjustment screws 219 and 221 fine adjustment of the examination lens 204 in the horizontal plane takes place.

Figure 16:
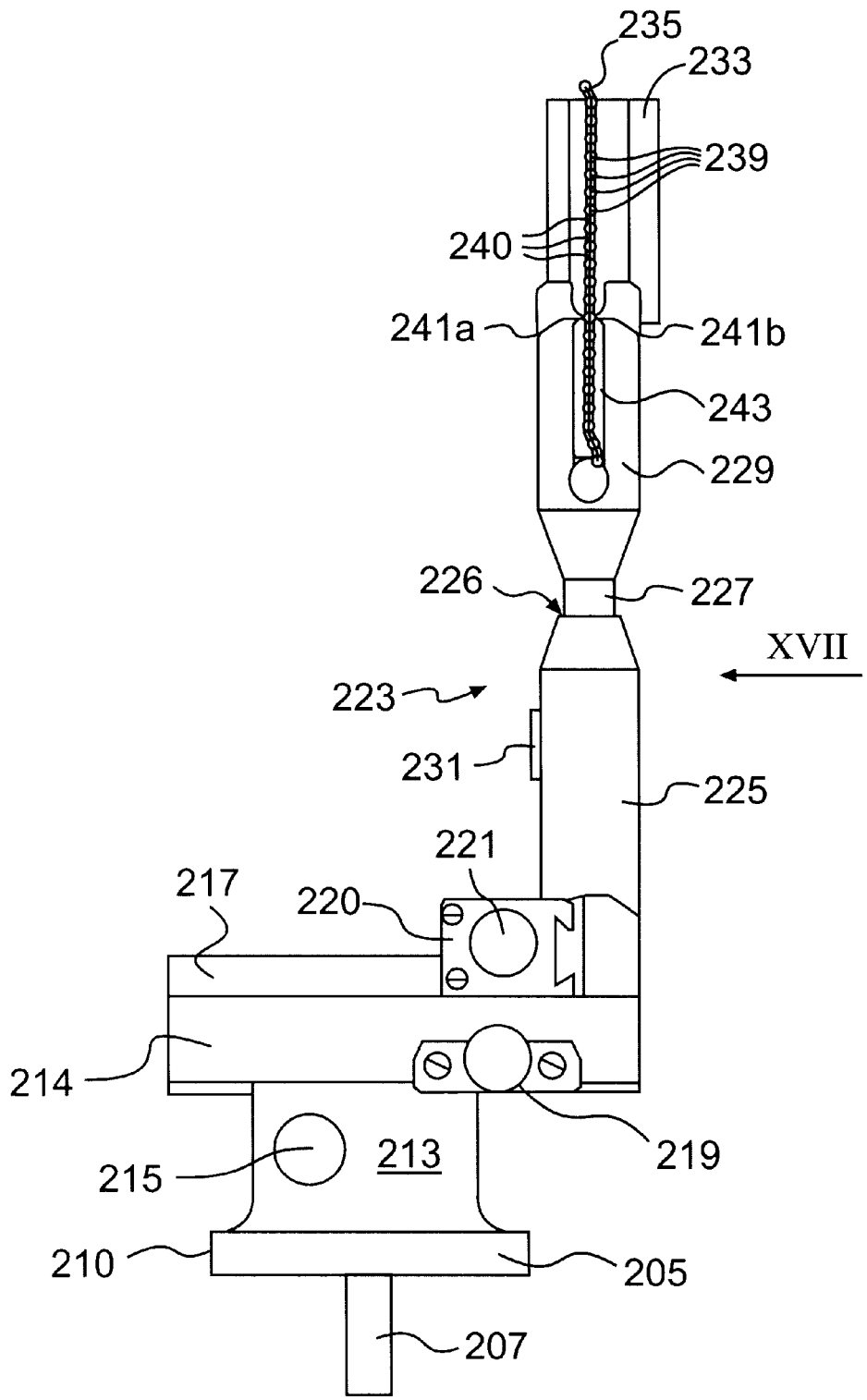
FIG. 16 shows the supporting unit which is shown in FIG. 15 as a separate accessory part in a larger representation.
Figure 17:
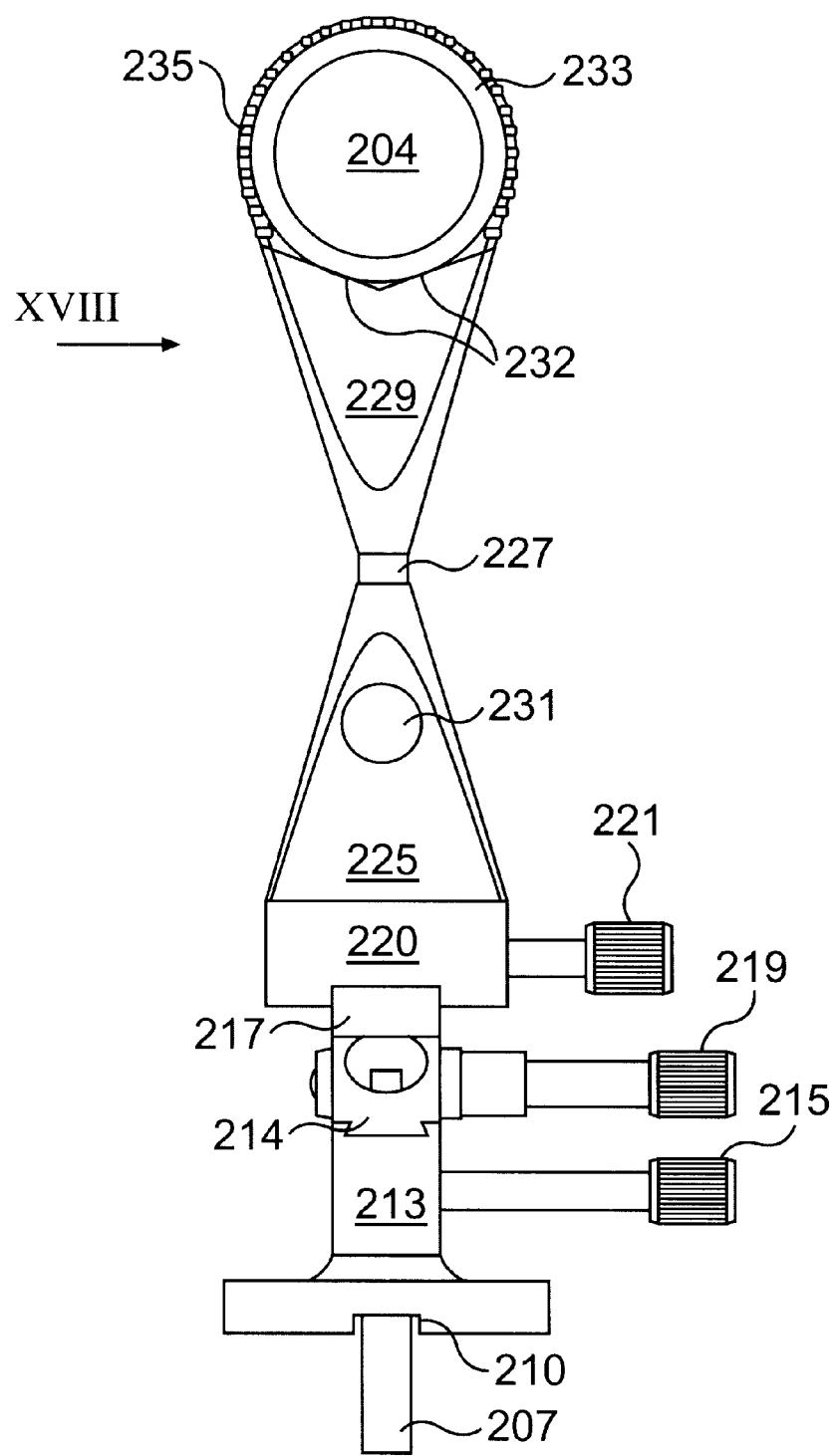
FIG. 17 shows the supporting unit which is shown in FIG. 16 in the viewing direction XVII there.
Figure 18:
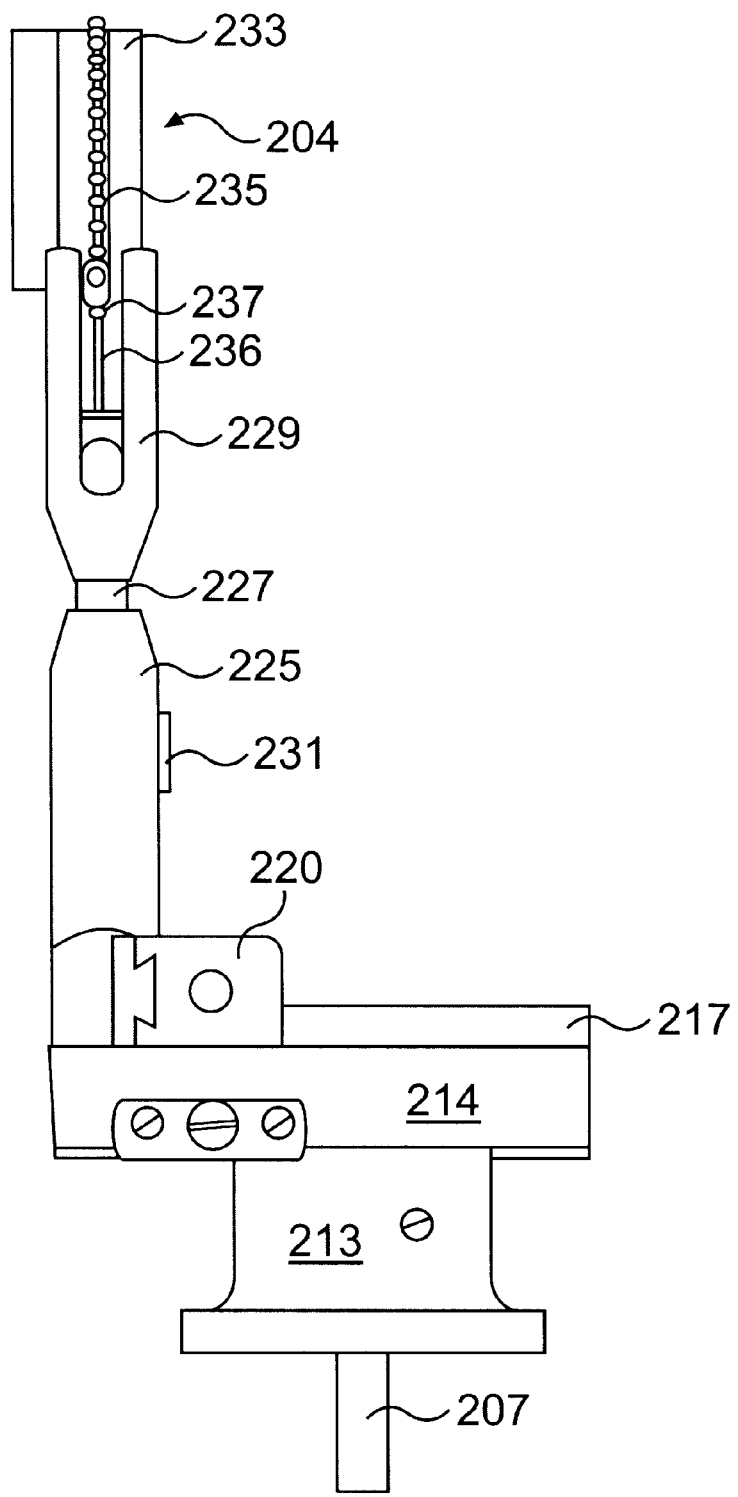
FIG. 18 shows the supporting unit which is shown in FIG. 17 in the viewing direction XVIII there.

For vertical height adjustment there is a two-part lens post 223 which on its top end bears the examination lens 204. The lower part 225 sits on the third carriage 220 and tapers prismatically upward. From the top end of the part 225 a blind hole 226 runs centrally into the part 225 in the axis of symmetry. In this blind hole 226 a mandrel 227 sticks which passes into the upper component piece 229 of the lens post 223. Proceeding from the mandrel projection, the component piece 229 widens prismatically upward. The mandrel 227 can be moved in the blind hole 226. The vertical height of the examination lens 204 is set manually by this motion. This height adjustment is self-locking based on a frictional force-fit. The self-locking is achieved by a permanent magnet which is captively located in the lower part 225 and which however can move in the direction to the surface of the mandrel 227. Since the mandrel 227 consists of ferromagnetic material, the permanent magnet in the mandrel 227 which has been inserted into the blind hole 226 is pulled against its surface and thus locks the vertical displacement by self-locking. But locking is only so strong that movement as a result of the inherent weight of the examination lens 204 plus its top component piece 229 is suppressed. But adjustment is possible manually. The location of the permanent magnet is apparent in FIGS. 16 to 18 by a disk-shaped mounting aid 231.

The examination lens 204 lies in a V-shaped recess 232 on the top end of the component piece 229 on its mount jacket 233. The examination lens 204 is held with a band-like flexible lens holding element 235 which has a chain-like structure. One end of the element 235 is held with a spring 236 roughly in the center on the end of the lateral lengthwise groove 237 of the component piece 229. The element 235 as a chain-like structure has nubs 239 which are equally spaced in the lengthwise direction and which are separated by intermediate spaces 240 with a thinner band cross-section. One of these intermediate spaces 240 is hooked between two projections 241a and 241b in a lateral lengthwise groove 243 on the side opposite the lateral lengthwise groove 237. The spring 236 tensions the lens holding element 235 and thus pulls the examination lens 204 into the recess 232 and fixes it. The lens holding element 235 can have a different structure, for example it can be made as a chain, compared to the nubs 239 and the narrow intermediate spaces 240. When using a chain likewise the two projections 241a and 241b could be present; then the chain would be suspended on its outer regions; but also there could be only a single projection into which one chain link at a time is suspended.

As detailed above, the lens supporting unit 203 is locked with the notch 210 and a sheet strip 211 which fits it on the holding unit 7. But equally well there could be other catch elements such as a pin which is arranged radially to the stud 207 and which fits into a corresponding hole in the holding unit 7. The locations of the pin and hole can of course be interchanged. Also textured surfaces can be used with structures which fit into one another.

In order to eliminate disruptive reflections in the examination and to deflect the path of the observation beam, the top part 229 of the lens post can be equipped with a tilting means for the examination lens 204. The tilting means can be a simple swivel axis. But preferably however three swivel joints spaced apart from one another can be used with swivel axes which run parallel to one another, i.e., there is a angle leg with an adjustable apex angle, and the other leg ends can in turn be swivelled with a swivel joint. On the topmost leg end the examination lens 204 is held with a swivelling capacity. With this arrangement tilting of the lens is possible with preservation of the center of the lens at a stipulated point in space.

By using the lens supporting unit 203 the physician can adjust the examination lens 204 optimally to the patient's eye 1 via its precision three-dimensional adjustment. After adjustment he has both hands free for the examination and treatment to be performed. He can also, especially using the video recording unit 46 and 70, undertake the corresponding documentation. Instead of the video recording unit a camera can also be flanged in order to undertake the corresponding documentation. Since the examination lens remains adjusted in its position by self-locking, at total rest the recording can be done with the choice of the image extract and sharpness adjustments.

Only the embodiment of the invention having the vertically running branch 20 of the holding unit 7 in a single column with the narrow column cross section allows optimum examination of the vitreous body and the ocular fundus using the examination lens 204 which is supported by the lens supporting unit 203. The lens supporting unit 203 can be used with the initially described, already known slit lamp device which has a three-column holding unit. Also, use together with other slit lamp devices is possible if a corresponding coupling is present.

What is claimed is:

1. A slit lamp device for stereoscopic examination of the eye of a patient with a viewing unit, and the eye can be illuminated with a light beam which proceeds from an illumination unit with a stipulated cross section, the illumination unit is located on top of a vertically running branch of a holding unit, the eye to be examined can be positioned in a roughly horizontally running plane on one side of the holding unit and the viewing unit is located roughly in the plane on the side of the holding unit opposite it, wherein the vertically running branch of the holding unit, which branch carries the illumination unit, is made in only one single column with the narrow column cross section on which there is a deflection mirror with which the emission of the illumination unit can be directed into or onto the eye, by which good patient-physician contact with only slight optical distortion between the viewing unit and the eye of the patient can be achieved.

2. The slit lamp device as claimed in claim 1, wherein the holding unit is made L-shaped, preferably in one piece, the illumination unit being located on one leg end and the area of the other end of the leg being held in a swivel joint which has a vertical swivel axis.

3. The slit lamp device and as claimed in claim 2, wherein the coupling is made as a locking plug coupling with a support part for resting on the holding unit, one coupling part of the coupling being made as a central axial hole to the vertical swivel axis of the holding unit, a matching stud of the lens supporting unit being made to be inserted into the axial hole, and the locking capacity being formed by at least one catch element with one catch component element each on the holding unit and another on the lens supporting unit, and the two component elements can be inserted into one another.

4. The slit lamp device as claimed in claim 1, further comprising by a second holding unit which is made L-shaped, in one piece, for the viewing unit, the viewing unit being located on one end of the leg and the area of the other end of the leg being held in a swivel joint which has a vertical swivel axis and especially the swivel axis for the holding units of the viewing unit and the illumination unit coinciding.

5. The slit lamp device as claimed in claim 1, wherein the holding unit for the illumination unit is made hollow inside with a cavity, a force transmission element for adjusting the cross section of a diaphragm opening in the illumination unit is guided in the cavity for producing a stipulated cross section of the thin streak of light and there is an adjustment element which acts on the force transmission element preferably at the origin of the leg of the first L-shaped holding unit.

6. The slit lamp device as claimed in claim 1, wherein the illumination unit has at least one optical filter which can be placed in the illumination beam, a blue and/or a gray filter and the viewing unit has at least one additional filter which can be placed in the viewing beam path, for example a yellow filter.

7. A slit lamp device for stereoscopic examination of the eye of a patient, as claimed claim 1, with a viewing unit, and the eye can be illuminated with a light beam which proceeds from an illumination unit with a stipulated cross section, the illumination unit is located on a vertically running branch of a holding unit, the eye to be examined can be positioned in a roughly horizontally running plane of one side of the holding unit and the viewing unit is located roughly in the plane of the side on the holding unit opposite it, further comprising a lens supporting unit which can attached and removed again without using tools manually via a locking plug coupling for an examination lens which then comes to rest in front of the inlet of the observation beam into the viewing unit in the observation beam path, and which is used especially to examine the vitreous body and the ocular fundus of the patient's eye, the examination lens is held self-locking with a turning capacity and self-locking in all three-dimensional directions with an adjustment capacity with the lens supporting unit, the supporting unit having no mechanical connection to the other devices adjacent to the device, such as a head and chin holder.

8. Lens supporting unit as an accessory part for a device as claimed in claim 1, comprising a coupling part with which the lens supporting unit can be manually placed without using tools on a holding unit for an illumination unit of a device as claimed in claim 1, by an examination lens, suited for examining the vitreous body and the ocular fundus of a patient's eye, by a two-part lens post with one part which can be moved against the other part with self-locking for vertical adjustment of the examination lens, and by a movement means for moving the lens post in two horizontal directions perpendicular to one another.

9. Lens supporting unit as claimed in claim 8, wherein one part of the lens post has a mandrel which can be moved with a clearance fit in one blind hole of the other part of the lens post, the mandrel consists of ferromagnetic material, in the blind hole there is a permanent magnet with limited motion which is thus captive, and which presses against the surface of the mandrel which has been pushed into the blind hole and thus keeps one part of the lens post in the position which has been set.

10. Lens supporting unit as claimed in claim 8, comprising a band-like lens holding element which has a chain-like structure, with its one end which is held to be tensionable in the lengthwise direction of the element on one part of the lens post with a spring element, by a lens support for the examination lens likewise on one part of the lens post and by a suspension element for the end area of the lens holding element which can be tensioned around the lens edge so that the examination lens can be easily replaced by another examination lens preferably with a different focal distance.

11. Lens supporting unit as claimed in claim 8, comprising a lens tilting unit for tilting the examination lens, the tilting unit having three swivel joints which are spaced apart from one another with swivel axes which are parallel to one another so that the lens center point can be kept at a stipulated point in space when the lens is tilted.

12. A slit lamp device for stereoscopic examination of the eye of a patient with a viewing unit which is made as a stereomicroscope, and the eye can be illuminated with a thin streak of light which proceeds from an illumination unit with a stipulated beam cross section, the illumination unit is located on a vertically running branch of a holding unit, the eye to be examined can be positioned in a roughly horizontally running plane on one side of the holding unit, and the viewing unit is located roughly in the plane on the side of the holding unit opposite it, wherein the stereomicroscope is a Greenough microscope which does not have a collimated (nonparallel) beam path, from at least one beam path of which a component beam can be masked out with a unit for coupling the image in/or out, the video information of the component beam is guided to a recording unit which is located in the viewing unit.

13. The slit lamp device as claimed in claim 4, wherein the recording unit is made to be inserted into the viewing unit or taken out of it, and decoupling of the component beam to the recording unit takes place by geometrical beam division.

14. A slit lamp device for stereoscopic examination of the eye of a patient, with a viewing unit which is made as a stereomicroscope, such as a Greenough microscope, and the eye can be illuminated with a thin streak of light which proceeds from an illumination unit with a stipulated cross section, the illumination unit is located on a vertically running branch of a holding unit, the eye to be examined can be positioned in a roughly horizontally running plane on one side of the holding unit, the viewing unit is located roughly in the plane on the side of the holding unit opposite it, as claimed in claim 1, wherein for positioning in the X and Y direction (i.e. in one horizontal plane) and in the Z-direction (vertical adjustment) of the thin streak of light which is to be directed into the patient's eye together with the viewing unit there is a guide lever, in its top are inserted signal-delivering elements, by their actuation the functions of the device and/or of the peripheral units which interact with the device can be controlled so that the examiner need not turn his gaze from the viewing unit and preferably manual adjustment actions can be done at the same time also with the hand operating the guide lever.

15. The slit lamp device especially as claimed in claim 14, an element which produces character information, and an optical coupling unit with which the image can be inserted into at least one beam path of the examination unit for observation with the eyepiece of the viewing unit and the video information preferably displays data which are changed or adjusted by actuating the guide lever.

* * * * *